United States Patent [19]

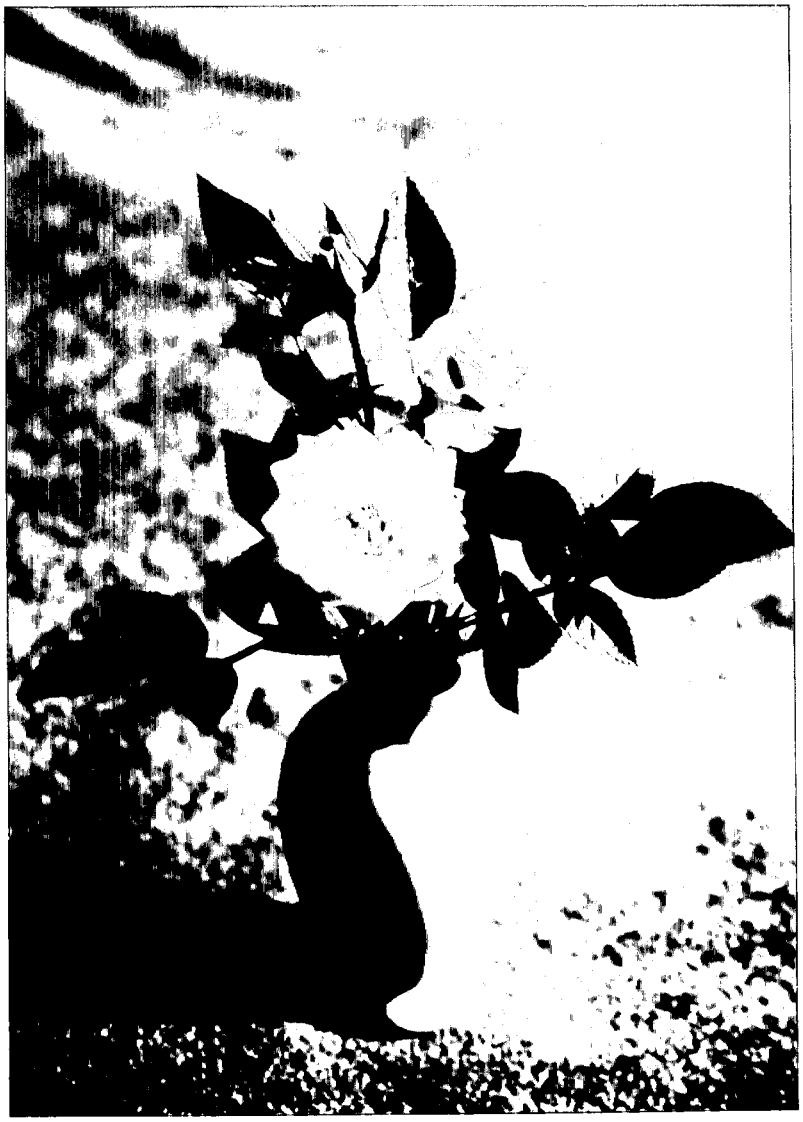

Bennett

[11] Patent Number: Plant 5,564

[45] Date of Patent: Oct. 1, 1985

[54] MINIATURE ROSE PLANT—FAIR DINKUM

[76] Inventor: Cecelia L. D. Bennett, 489 Minot Ave., Chula Visat, Calif. 92010

[21] Appl. No.: 575,188

[22] Filed: Jan. 30, 1984

[51] Int. Cl.[4] ..... A01H 5/00

[52] U.S. Cl. ..... Plt./7

[58] Field of Search ..... Plt./7

*Primary Examiner*—Robert E. Bagwill

[57] ABSTRACT

The subject of the present disclosure is a new and distinct variety of miniature rose plant characterized by it's pink petals, ranging from soft shades of Spinel Pink to deepending shanks of Rose Opal a the edges.

1 Drawing Figure

The present invention relates to a new and distinct variety of a hardy, dwarf, miniature bush plant of the miniature class; the variety being primarily characterized as a pink blend.

The variety is further characterized by:

Long stemmed exhibition-quality blooms, borne singly or in sprays , held very erect and well above the foliage.

Has a very slight fragrance.

The plant ranges in height from 12 to 36 inches. The branches are sturdy and erect, heavily branched with medium foliage covering. The plant is a moderate to heavy bloomer that does well in either the green house or outdoors.

The plant is very vigorous with good growth habits, well shaped and attractive in appearance, bearing numerous leaflets of average size.

The seed parent was an unnamed seedling of unknown parentage, and the pollen parent was Coral Treasure (Miniature Rose Plant, orange blend; R. S. Moore; introduced by Sequoia Nursery, 1971).

Subsequent to the origination of the variety, I have successfully reproduced it at Tiny Petals Nursery located at aforesaid retainingthe distinguishing characteristics through succeeding propagations by cuttings.

The descriptive matter which follows pertains to roses grown and color values observed in plants and newly opened blooms in the months of April through June. The plants were grown outdoors in Chula Vista, Calif., and are believed to be accurate standards for this same cultivar in similar conditions of soil and climate elsewhere.

The color photograph illustrates the variety.

Referring now specifically to the new and distinct variety of miniature rose plant, the following is a detailed description thereof in outline; all major color plate identifications being by reference to The British Colour Council Horticultural Colour Chart, except where common terms of color definition are employed.

Type: Hardy, dwarf, bushy, green house or outdoor, garden decoration and exhibition-quality potted plant.

Class: Miniature.

Variety name: Fair Dinkum

Flowers borne: One to a stem or in sprays of 3 to 5 or more on erect stems with foliage well below the blooms.

Quantity of bloom: Moderate to heavy both outdoors and green house grown.

Bud:

*Peduncle.*—Medium to long (averaging 25 to 35 mm); average diameter and sturdy; medium green with some tinting of bronze.

*Hairs.*—Extremely small and delicate; very numerous; bronze in color; located over the entire surface of the peduncle and outer surface of sepals, but not on the calyx tube.

*Calyx.*—Color is Pod Green (061/1 page 120) with some tinting of bronze near the middle of the sepals.

*Opening.*—Opens well in all weather.

Bloom:

*Size when fully open.*—averaage for a miniature variety40 to 45 mm (1¾").

*Petalage.*—Double — Averaging about 20 to 30 petals, arranged regularly plus petaloids (8 to 12 or more).

*Form.*—Urn-shaped to ovoid as the bloom progresses. The petals remain at first somewhat tightly cupped with the tips and/or margins reflexed outward, becoming later at maturity more loosely cupped, with tips and/or margins reflexed outward. The outermost row of petals at the fully opened stage will reflex at their margins, rolling under from the apex of the petal on both sides. When viewed from the top, the outermost petals give the appearance of five-pointed star. The rest of the petals retain a broad obovate appearance.

Petals: Fairly thick with good substance and a matter finish.

*Shape.*—Outer petals are of a broad obovate form with a slight peak at the apex. The intermediate petals are very much like the outer petals only narrower. The inner petals are narrower obovate form; very little different between intermediate and inner petals noticeable. The petaloids are like small lanceolates with occasional irregularities in shape.

Color: Newly opened flowers from plants grown outdoors (June 1983), Chula Vista, Calif.

*Outside petals.*—Upper surface — Rose Opal (022 page 110) at the edge with gradually paling shades of Spinel Pink in the center of the petals (0625/2 to 0625/3 page 184) and Naples Yellow (403/3 page 121) at the base. Under Surface — Narrow edge of Rose Opal (022 page 110) with gradually paling shades of Spinel Pink in the center (0625/2 to 0625/3 page 184) and a larger base of Naples Yellow (403/3 page 121) than the upper surface, reaching almost to the middle of the petals.

*Intermediate petals.*—Same as outside petals in all color qualities.

*Inner petals.*—Same as outside petals in all color qualities.

*General color effect.*—Newly opened flowers — Soft shades of Spinel Pink ith deep margin of Rose Opal on every petal. Two days to a week open — Color shows very slight paling of original colors; barely noticeable change. Spent petals drop off cleanly, except occasional petaloids.

*Flower longevity.*—(May and June 1983) Plant in pot 6 to 8 days from bud with sepals down to fully open bloom. Holding at fully open with barely any noticeable fading of color for additional 5 to 8 days before dropping petals. Cut blooms at livingroom temperature 4 to 5 days or longer from bud to open bloom.

Reproductive organs:

*Stamens.*—A generous amount arranged uniformly around the pistil.

*Filament.*—Varying in lengths; reddish in color.

*Pollen.*—Abundant.

*Pistil.*—Short, abundant and spreading.

*Styles.*—Varying in lengths; reddish in color.

*Ovaries.*—All encased in calyx.

*Hips.*—Some.

*Seed.*—Few or none.

*Sepals.*—Permanent; spear-shaped; open as bloom opens, but do not recurve against the peduncle.

Foliage:

*Leaves.*—Five to seven, average size for a miniature rose plant.

*Leaflets.*—Broad ovate-shaped.

*Margin.*—Very serrated with occasional reddish tinge on the edge, usually present on the newer foliage.

*Color.*—Ranging from Fern Green (086/2 page 186) with a tinge of bronze in the newer leaves to Spinach Green (0960/2 page 187) in the mature leaves. The under surfaces have a matte finish of a slightly lighter color than the upper surface.

*Rachis.*—Medium strength; upper side is grooved and may have a few small hairs; under side is smooth except for a few sparse throns.

*Stipules.*—Varying in length from samll to medium; average width; tapering auricles angled outward at about 45 degrees.

Growth:

*Habit.*—Dwarf; bushy; much branched; average to large for a miniature rose plant.

*Growth.*—Vigorous.

*Canes.*—Medium; sturdy; held very erect.

*Main stems.*—Color — Spinach Green (0960/2 page 187) to Spinach Green (0960/3 page 187) with some tinting of bronze, especially noticeable on the newer stems.

*Thorns.*—Few if any on the main stems and branches; reddish with a pale yellow tip in the larger thorns; pale yello to pale green in the smaller thorns. Pale yellow to pale green, very small and slender throns present on the under side of the rachis, but only sparsely.

*Branches.*—Color — Spinach Green (0960/2 page 187) to Spinach Green (0960/3 page 187) with some tinting of bronze. Medium to long in length; sturdy; very erect. Thorns — Few or none; hooked slightly downward. Prickles — None. Hairs — none.

The miniature rose plant and its flowers as herein described may vary in slight detail due to climatic, soil, and cultural conditions under which the variety may be grown; the present description being of the variety as grown at Chula Vista, Calif.

The following is claimed:

1. A new and distinct variety of miniature rose plant of hardy, dwarf, bushy, much branched habit, substantially as illustrated and described, characterized by its pink petals with a deeper pink margins and vigorous growth habit, easy to propagate from cuttings, with flowers borne singly and in aprays of 3 to 5 or more.

* * * * *